(12) United States Patent
Wong

(10) Patent No.: US 8,470,268 B2
(45) Date of Patent: Jun. 25, 2013

(54) ORAL FLUID COLLECTOR

(76) Inventor: Johnson N. S. Wong, Rolling Hills, CA (US)

( * ) Notice: Subject to any disclaimer, the term of this patent is extended or adjusted under 35 U.S.C. 154(b) by 15 days.

(21) Appl. No.: 13/149,629

(22) Filed: May 31, 2011

(65) Prior Publication Data

US 2012/0308448 A1    Dec. 6, 2012

(51) Int. Cl.
| | | |
|---|---|---|
| *B01L 3/00* | (2006.01) |
| *B01L 3/14* | (2006.01) |
| *B65D 81/00* | (2006.01) |
| *B01D 35/00* | (2006.01) |
| *C12M 3/00* | (2006.01) |
| *B65D 69/00* | (2006.01) |

(52) U.S. Cl.
USPC ........... 422/558; 422/547; 422/549; 422/557; 600/573; 435/288.1; 210/437; 206/569

(58) Field of Classification Search
USPC . 422/547, 549, 554–560; 600/573; 435/288.1
See application file for complete search history.

(56) References Cited

U.S. PATENT DOCUMENTS

| | | | | |
|---|---|---|---|---|
| 4,920,975 A | * | 5/1990 | Fay ............................. | 600/573 |
| 2010/0140182 A1 | * | 6/2010 | Chapman et al. ............ | 210/741 |

FOREIGN PATENT DOCUMENTS

WO    WO 2004021964 A2 *   3/2004

* cited by examiner

*Primary Examiner* — Bobby Ramdhanie
*Assistant Examiner* — Jennifer Wecker
(74) *Attorney, Agent, or Firm* — Berliner & Associates

(57) ABSTRACT

An apparatus for collecting oral fluid, comprising a vial formed with an inner specimen receptacle for receiving the oral fluid. The open top of the vial is cylindrical and formed with threads on a portion of its outer surface adjacent its open top. The specimen receptacle is disposed within the vial, spaced along its length from the inner surface of the vial and has a closed bottom end and an open top end. The entire periphery of the receptacle top end is sealingly secured to the inner surface of the vial proximal to but spaced from the vial's open threaded end. The bottom end of the vial can be open and flat and extend beyond the closed end of the specimen receptacle to enable the vial to be set on a horizontal surface. A funnel is removably placed in the open top end of the vial and narrows to an inner neck fits within the open top end of the vial. An outer neck depends from the funnel to surround the inner neck and extend beyond the inner neck and beyond the threaded portion of the outer surface of the vial to provide protection for the threaded portion of the vial from contamination from collected oral fluid. A cap for the vial is retained securely inside an enclosure on the underside of a lid that frictionally but removably fits to the top end of the funnel.

10 Claims, 4 Drawing Sheets

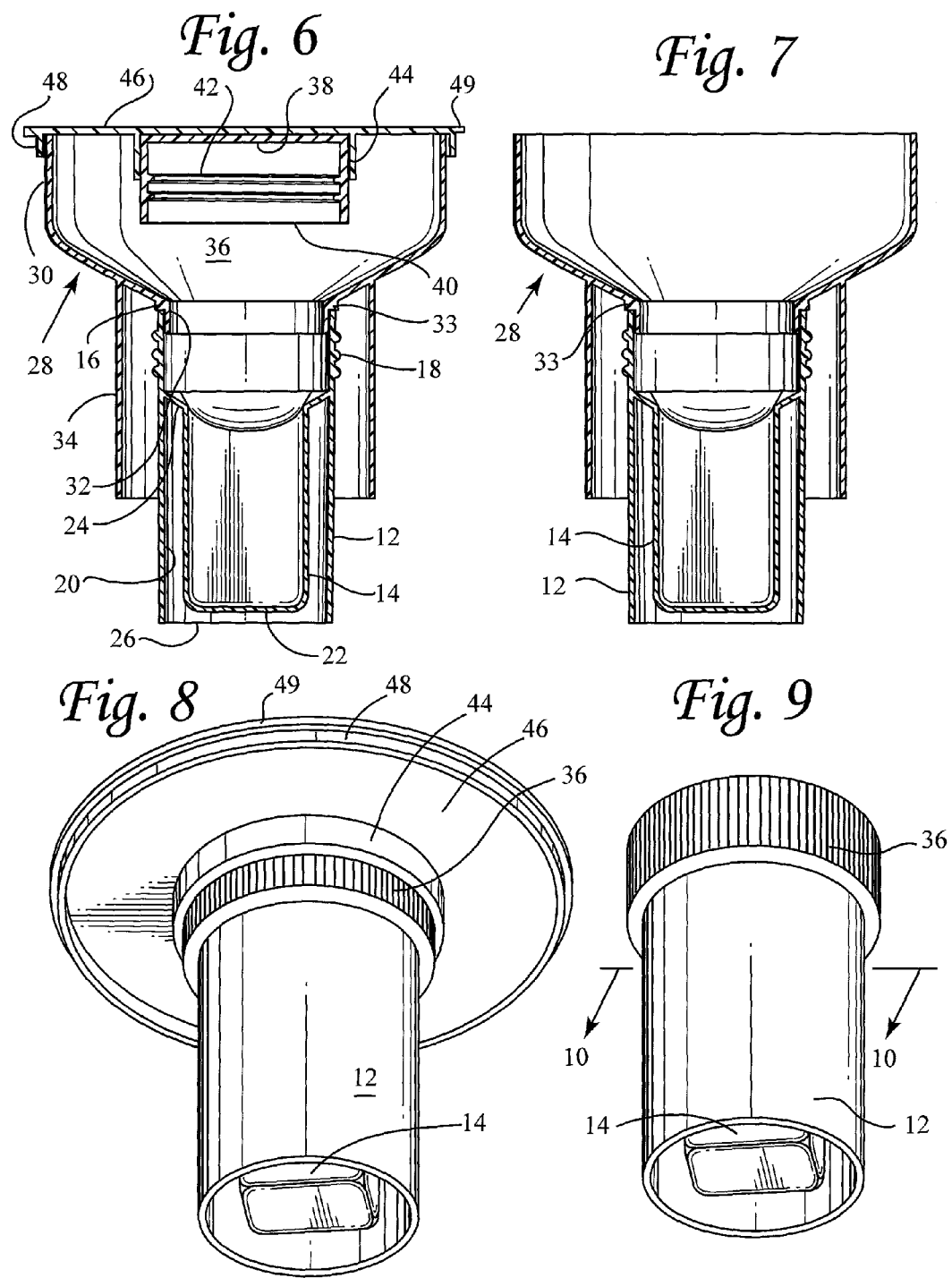

ORAL FLUID COLLECTOR

FIELD OF THE INVENTION

The present invention is directed to medical and laboratory equipment, more specifically, to an apparatus for collecting oral fluids.

BACKGROUND OF THE INVENTION

With the many problems associated with urine collection for drug testing, including difficulties involved in monitoring the collection, urine adulterants, "shy bladder" syndrome, and many others, oral fluid (saliva) emerges as a promising specimen for drug testing, because:
  (1) the specimen can be collected easily, and under direct supervision, avoiding many of the collection problems associated with urine collection,
  (2) because oral fluids are a filtrate of blood, the oral fluid-drug concentration should reflect blood-drug concentrations, instead of urine drug concentrations,
  (3) there are very few adulterants associated with oral fluid collections, making the drug test results more reliable, and
  (4) oral fluids can be used for testing by using most of the conventional screening and confirmation methods.

However, the drugs present in oral fluids are usually not protein bound and therefore easily attach to the surface matrix of the collection devices. The technique and materials used to collect oral fluid affect the drug concentration, and different drugs may have different affinities for the collection materials. The materials for both the collection tube and the fluid absorbent used must be selected to minimize the surface bonding of the drug(s) to be detected. To date, there is no generally recognized standard for the method, the volume of specimen required, the absorbent used for collection, the material used for the collection tube, and the time interval needed to collect oral fluid specimens.

There have been a variety of methods and devices used to collect oral fluid (saliva) specimens, and some commercially available collection devices. A report prepared for the National Institute of Justice, the US Department of Justice, on "Evaluation of Saliva/Oral Fluid as Alternate Drug Screen Specimen," authored by Dennis Crouch et al., at http://www.ncjrs.gov/pdffiles1/nij/grants/203569.pdf, deals primarily with the use of oral fluid as an alternate drug testing specimen, and the effects of collection devices on drug concentration. Nonstimulated saliva can be collected by a simple draining (drooling) method, in which saliva is allowed to drip from the mouth into a collection container. The collection time may be up to 10 minutes in order to collect sufficient amount for testing. Saliva production can be stimulated by:
  (1) simple cheek and tongue movements,
  (2) chewing on a piece of inert material such as paraffin wax, rubber band, or chewing gum,
  (3) sucking on a lemon drop or a small amount of citric acid.
Following stimulation by one of the above methods, the oral fluid produced can be sucked up using a syringe or swabbed from the mouth. The collection time is usually 2 to 5 minutes.

Commercially available devices usually use a combination of mechanical stimulation and collection using some absorbent materials such as cotton balls, weaved polyester pads, or sponges. The absorbent material piece is gently chewed in the mouth in order to stimulate the production of saliva and to absorb the saliva produced. After the absorbent material is saturated with the saliva, it is removed from the mouth and the saliva is extracted by squeezing through a syringe, or by centrifugation. The following are descriptions of various saliva collection devices, some of which may be historic and no longer available.

The UltraSal-2™ (Oasis Diagnostics) saliva collection device, at http://www.4saliva.com/products/ultrasal.php, is for the collection of oral fluid/saliva samples. It automatically splits the saliva specimen into two aliquots in separate collection tubes. One tube can be used for testing while the second may be used for confirmation of results or for future use. No absorbent is involved in this method. The specimen is collected by holding the mouth piece between the lips and expectorating the oral fluid through the hole in the mouth piece into the collection tubes. The process is stopped when there is sufficient specimen collected. The collection tubes are capped and the mouthpiece is discarded. The volume collected is up to the capacity of the tube; the volume recovered is 100% of the collected volume.

The Versi-Sal (Oasis Diagnostics), at http://www.4saliva.com/products/versisal.php, is a fluid collection device that incorporates a proprietary interchangeable absorbent pad. It works by placing the device pad under the tongue and collecting saliva until a novel sample sufficiency indicator is triggered, taking 1-2 minutes. The collector is then pushed down into a supplied compression tube until the pad is significantly compressed to release the absorbed saliva. The saliva specimen is forced through an outlet into a graduated tube. Recovery efficiency is about 60%.

In the Salivette® (Sarstedt) device, at http://www.sarstedt.com/pdf/katalog/en/SARSTEDT_E_0409%2042.pdf, saliva collection is carried out by chewing a cotton wool swab. Recovery of the saliva sample is achieved by returning the swab to the Salivette® tube and centrifuging the container. The volume collected is 1.7 ml; the volume recovered is 1.4 ml (82%).

In the Intercept (STC) device, a pad is swabbed in the mouth for 2 to 5 minutes, the pad is inserted into a vial and snapped off at a scoring, and the vial is capped and sealed. Others devices mentioned in the literature, including: OraSure (Epitope), Saliva Sampler (Saliva Diagnostics) and ORALscreen collector (Avitar)

There are also available several devices incorporating saliva/oral fluid collection together with drug screen testing. In some systems, the collection device is provided along with a separate drug testing strip. In others, the collection part of the system is integrated with the testing part, and the oral fluid specimen goes directly onto the testing strip. The VerOFy® (Oasis Diagnostics), at http://www.4saliva.com/products/verofy.php, incorporates rapid and standardized saliva collection with immunochromatographic test strips providing a system for delivery of immediate results in the field or at point-of-care locations. The Oraline-SalivaConfirm™ Oral Fluid Drug Test provides a simple at-home saliva collection procedure to screen for the four most popular drug classes (: mAMP, COC, OPI, THC) to determine recent usage.

Saliva QuikScreen, at http://www.spyville.com/saliva-drug-testing-kit.html, is a saliva drug test kit for opiates, marijuana, methamphetamines, and cocaine. The collection kit appears to include an absorbent pad at the tip of a syringe plunger and a syringe barrel.

It is important during the collection and handling of biological specimens to minimize specimen contamination and infection. Providing the collection apparatus in sterile packages minimizes contamination prior to use, but there still remains the potential of specimen contamination during the collection process. Moreover, sterile packaging does not reduce the potential of infection to medical personnel who handle or otherwise come into contact with the specimen vial. The present inventor is a co-inventor of a specimen collector described in U.S. Pat. No. 4,741,346 that overcomes such drawbacks. It is an apparatus for collecting biological fluids, such as sputum, that includes a specimen vial in which a funnel is inserted and which is held in a substantially upright position in a base. The base has a detachable lid that houses and holds a vial cap and which is graspable to be used to secure the cap to the vial.

BRIEF SUMMARY OF THE INVENTION

While the apparatus of U.S. Pat. No. 4,741,346 enables a significant degree of isolation of the collected specimen, the present invention provides apparatus with at least the same isolation of the specimen but with a more compact design, with fewer parts, and therefore less costly. It is particularly suitable for collecting oral fluids, such as saliva for drug testing or other clinical procedures, with a maximum degree of isolation while minimizing contamination and the possibility of infection of handlers. In addition, if a candidate's saliva tests positive, the capped vial of the same apparatus can be used for mailing without changing the container.

More particularly, the present invention provides an apparatus for collecting oral fluid, comprising a vial formed with an inner specimen receptacle for receiving the oral fluid. At least the open top of the vial is cylindrical and formed with threads on a portion of its outer surface adjacent its open top. In a particular embodiment, the specimen receptacle is rectangular in cross-section and disposed within the vial, spaced along its length from the inner surface of the vial. The specimen receptacle has a closed bottom end and an open top end. The entire periphery of the receptacle top end is sealingly secured to the inner surface of the vial proximal to but spaced from the vial's open threaded end. In a particular embodiment, the bottom end of the vial is open and flat and extends beyond the closed end of the specimen receptacle, to enable the vial to be set on a horizontal surface.

A funnel is removably placed in the open top end of the vial. It is formed with a wide, cylindrical open top narrowing to an inner neck at its bottom end which fits frictionally within the open top end of the vial. An outer neck depends from the funnel to surround the inner neck and extend beyond the inner neck and beyond the threaded portion of the outer surface of the vial. The outer neck provides protection for the threaded portion of the vial from contamination from collected oral fluid. A cap for the vial has a closed top end and an open bottom end with threads on its inner surface to mate with the threads on the outer surface of the vial. The cap is retained securely inside an enclosure on the underside of a lid that frictionally but removably fits to the top end of the funnel. With the lid removed, oral fluid can be directed into the funnel which further directs it into the specimen receptacle. After collection of the oral fluid, the lid, holding the cap with its threaded open end outwardly disposed, facilitates placing the cap onto the top of the threaded end of the vial to thread the cap onto the vial to close it, following which the closed vial can be separated from the lid.

BRIEF DESCRIPTION OF THE DRAWINGS

For a more complete understanding of the present invention, reference is now made to the following descriptions taken in conjunction with the accompanying drawing, in which:

FIG. 6 is a cross-sectional view of the collector taken on line 6-6 of FIG. 3;

FIG. 7 is a cross-sectional view of the collector similar to that of FIG. 6 but shown with the lid removed;

FIG. 8 is a bottom perspective view of the lid holding the cap while threading it onto the vial;

FIG. 9 is a bottom perspective view of the vial sealed by the cap;

DETAILED DESCRIPTION OF THE INVENTION

Figure 1:
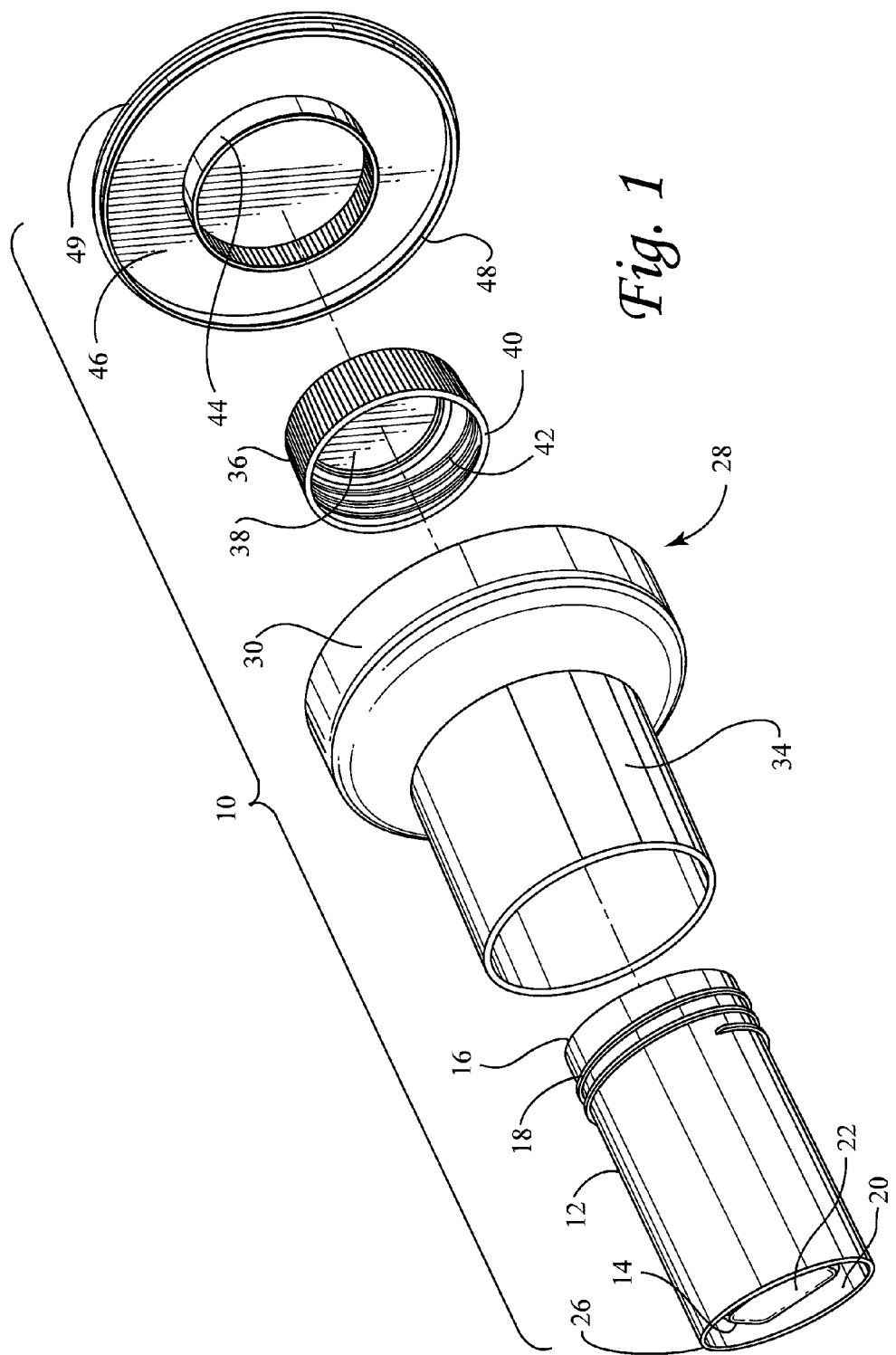
FIG. 1 is an exploded perspective view of the oral fluid collector in accordance with an embodiment of the invention, showing its components comprising a vial, a funnel, a cap for the vial, and a lid having an enclosure for retaining the cap.
Figure 2:
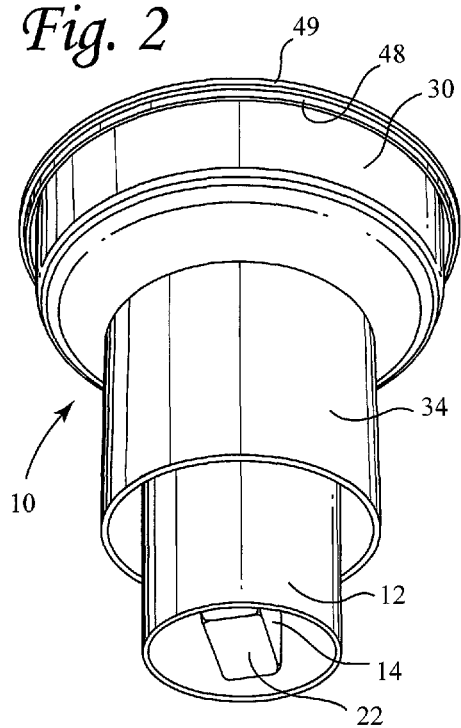
FIG. 2 is a bottom perspective view of the collector illustrated in FIG. 1.
Figure 3:
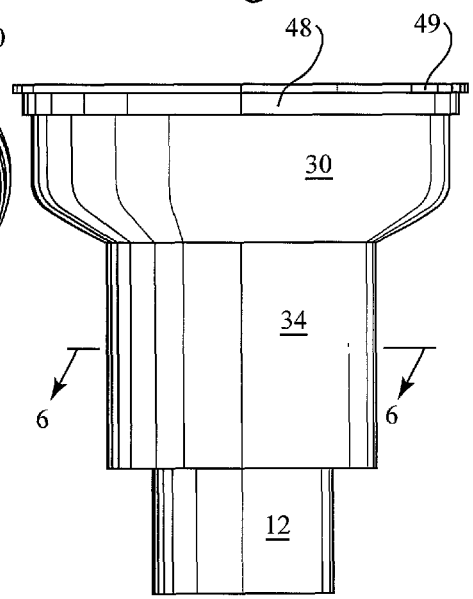
FIG. 3 is an elevational view of the collector.
Figure 4:
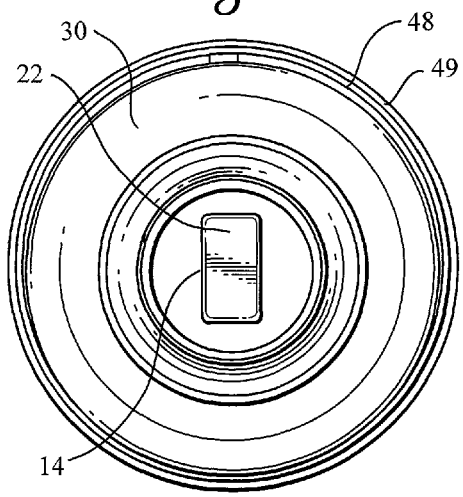
FIG. 4 is a bottom plan view of the collector.
Figure 5:
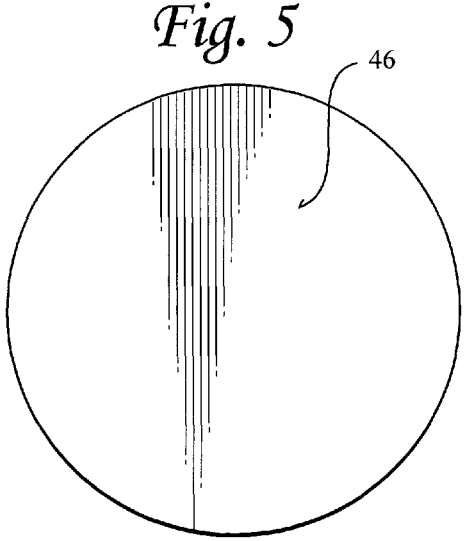
FIG. 5 is a top plan view of the collector.
Figure 10:
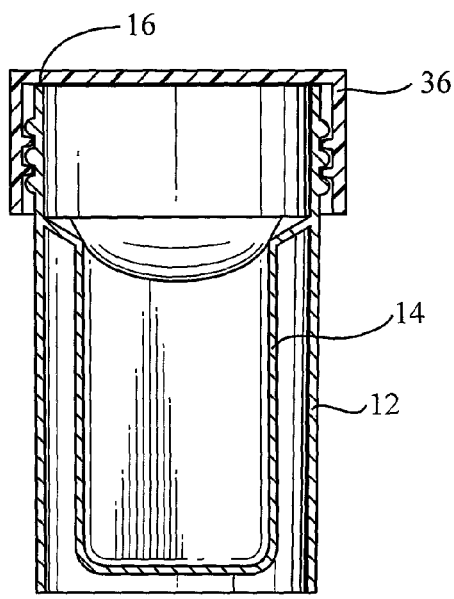
FIG. 10 is a cross-sectional view of the vial and cap taken on line 10-10 of FIG. 9.
Figure 11:
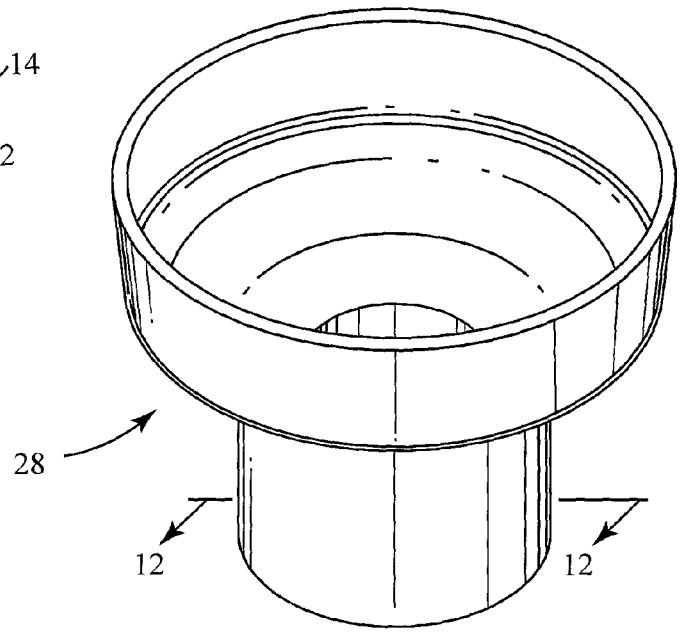
FIG. 11 is a top perspective view of the funnel and with FIG. 10 shows all the components of the oral fluid collector after use.
Figure 12:
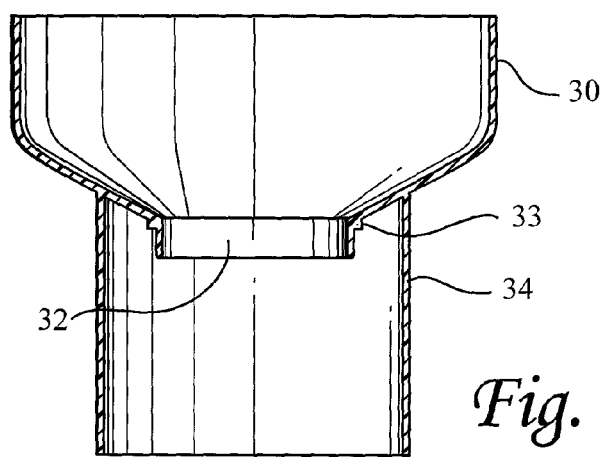
FIG. 12 is a cross-sectional view of the funnel of FIG. 11.

Referring to FIGS. 1 and 6, the components of an apparatus 10 of this invention for collecting oral fluid is shown. It comprises a vial 12 formed with an inner specimen receptacle 14 for receiving the oral fluid. At least the open top end 16 of the vial 12 is cylindrical and formed with threads 18 on a portion of its outer surface adjacent the open top 16. In a particular embodiment, the specimen receptacle 14 is rectangular in cross-section and disposed within the vial 12, spaced along its length from the inner surface 20 of the vial 12. The specimen receptacle 14 has a closed bottom end 22 and an open top end 24 (FIG. 6). The entire periphery of the receptacle top end 24 is sealingly secured to the inner surface 20 of the vial 12 proximal to but spaced from the vial's open threaded end 16. In a particular embodiment, the bottom end 26 of the vial is open and flat and extends beyond the closed end 22 of the specimen receptacle 14, to enable the vial to be set on a horizontal surface.

A funnel 28 is removably placed in the open top end 16 of the vial 12. It is formed with a wide, cylindrical open top 30 narrowing to an inner neck 32 (FIG. 6) at its bottom end which fits frictionally within the open top end 16 of the vial 12. An outer neck 34 depends from the funnel 28 to surround the inner neck 32 and extend beyond the inner neck 32 and beyond the threaded portion 18 of the outer surface of the vial 12. The outer neck 34 provides protection for the threaded portion 18 of the vial 12 from contamination from collected oral fluid.

A cap 36 for the vial 12 has a closed top end 38 and an open bottom end 40 with threads 42 on its inner surface to mate with the threads 18 on the outer surface of the vial. The cap 36 is retained securely inside an enclosure 44 centrally located on the underside 46 of a lid 49 having a lip 48 that that frictionally but removably fits the cap 36 to the top end 30 of the funnel 28.

Referring to FIG. 7, with the lid 49 removed, oral fluid can be directed into the funnel 28 which further directs it into the specimen receptacle 14 component of the vial 12. Referring to FIGS. 8-11, after collecting the oral fluid in the specimen receptacle 14, the funnel 28 is removed from the vial 12 and the lid 49 is removed from the funnel 28. While holding the cap 36 in the cap enclosure 44 with its threaded open end 40 outwardly disposed, the lid 49 facilitates placing the cap 36 onto the top of the threaded end 16 of the vial 12 to thread the cap 36 onto the vial 12 to close it. By such means a user can thread the cap 36 onto the vial 12 without coming into contact with the cap 36 or the open end 16 of the vial 12 until the vial 12 is sealed with the cap 36. The vial 12 sealed with the cap 36 threaded onto the top end 16 of the vial 12 can be separated from the lid 46 and is in condition to be shipped to a laboratory for analysis of the oral fluid specimen.

The entire oral fluid collector can be formed of commercially available polymer that will not add to or subtract from the oral fluid, such as saliva. A particularly suitable polymer is polypropylene. The prior art is quite familiar with the use of such materials in forming a wide variety of clinical and drug testing devices.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims.

The invention claimed is:

1. An apparatus for collecting oral fluid, comprising;
 a vial formed with an inner specimen receptacle for receiving the oral fluid, the vial having an open cylindrical top end formed with threads on a portion of its outer surface adjacent its top end, the specimen receptacle being spaced along the length of its outer surface from the inner surface of the vial and having a closed bottom end and an open top end, the entire periphery of the receptacle top end sealingly secured to the inner surface of the vial proximal to but spaced from the open first end of the vial;
 a funnel which can be removably placed in the open top end of the vial formed with a wide, open top end narrowing to an inner neck at its bottom end which fits within the open top end of the vial, the specimen receptacle terminating at its open top end below but adjacent to the bottom end of the inner funnel neck, the funnel being formed with an outer neck depending from the funnel to surround the inner neck and extend beyond the inner neck and beyond the threaded portion of the outer surface of the vial to provide protection for the threaded portion of the vial from contamination from collected oral fluid; and
 a cap for the vial having a closed top end, an open bottom end, and threads on its inner surface to mate with the threads on the outer surface of the vial;
 whereby when assembled, oral fluid can be directed into the funnel and from there to the receptacle, whereupon the cap can then be threaded onto the receptacle to enclose the oral fluid.

2. The apparatus of claim 1 in which the bottom end of the vial is open and flat and extends beyond the closed end of the specimen receptacle to enable the vial to be set on a horizontal surface.

3. The apparatus of claim 1 in which the top end of the funnel and the inner and outer neck are cylindrical.

4. The apparatus of claim 1 in which the specimen receptacle is rectangularly shaped.

5. The apparatus of claim 1, including a lid formed to frictionally but removably fit to the top end of the funnel facing the specimen receptacle and carrying an enclosure for frictionally retaining the top end of the cap, whereby when the lid is removed, said oral fluid can be directed into the funnel, and whereby after oral fluid is received by the receptacle, the lid can, by holding the cap, facilitate placement of the cap onto the top of the vial and threading thereon to close the vial and thereafter be separated from the lid.

6. The apparatus of claim 5, in Which the cap enclosure is centrally located on the bottom surface of the lid.

7. An apparatus for collecting oral fluid, comprising; a vial formed with an inner specimen receptacle with an open top end and a closed bottom end for receiving the oral fluid, the vial having an open cylindrical top end formed with threads on a portion of its outer surface adjacent its top end and having an open and flat bottom end that extends beyond the closed end of the specimen receptacle to enable the vial to be set on a horizontal surface, the specimen receptacle being spaced along the length of its outer surface from the inner surface of the vial and having a closed bottom end and an open top end, the entire periphery of the receptacle top end sealingly secured to the inner surface of the vial proximal to but spaced from the open first end of the vial;
 a funnel which can be removably placed in the open top end of the vial formed with a wide, open top end narrowing to an inner neck at its bottom end which fits within the open top end of the vial, the specimen receptacle terminating at its open top end below but adjacent to the bottom end of the inner funnel neck, the funnel being formed with an outer neck depending from tile funnel to surround the inner neck and extend beyond the inner neck and beyond the threaded portion of the outer surface of the vial to provide protection for the threaded portion of the vial from contamination from collected oral fluid; and
 a cap for the vial having a closed top end, an open bottom end, and threads on its inner surface to mate with the threads on the outer surface of the vial;
 whereby when assembled, oral fluid can be directed into the funnel and from there to the receptacle, whereupon the cap can then be threaded onto the receptacle to enclose the oral fluid.

8. The apparatus of claim 7 in which the top end of the funnel and the inner and outer neck are cylindrical.

9. The apparatus of claim 7 in which the specimen receptacle is rectangularly shaped.

10. The apparatus of claim 7, including a lid formed to frictionally but removably fit to the top end of the funnel facing the specimen receptacle and carrying
 an enclosure centrally located on the bottom surface of the lid for frictionally retaining the top end of the cap, whereby when the lid is removed, said oral fluid can be directed into the funnel, and whereby after oral fluid is received by the receptacle, the lid can, by holding the cap, facilitate placement of the cap onto the top of the vial
 and threading thereon to close the vial and thereafter be separated from the lid.

* * * * *